United States Patent [19]

Naruse et al.

[11] Patent Number: 5,218,666
[45] Date of Patent: Jun. 8, 1993

[54] LIGHT OPERATED MECHANICAL ACTUATOR

[75] Inventors: Yoshihiro Naruse, Ichikawa; Tomokimi Mizuno, Chiryu; Mitsuhiro Ando, Tokyo; Naomasa Nakajima, Chofu, all of Japan

[73] Assignee: Aisen Seiki Kabushiki Kaisha, Kariya, Japan

[21] Appl. No.: 838,097

[22] Filed: Feb. 20, 1992

Related U.S. Application Data

[63] Continuation-in-part of Ser. No. 764,677, Sep. 25, 1991.

[30] Foreign Application Priority Data

Sep. 26, 1990 [JP] Japan ................... 2-256400
Feb. 21, 1991 [JP] Japan ................... 3-027069

[51] Int. Cl.[5] ............................................. G02B 6/00
[52] U.S. Cl. ........................................................ 385/147
[58] Field of Search ............... 385/147, 900, 31, 38, 385/115; 251/11; 126/417; 337/298, 306, 320, 327

[56] References Cited

U.S. PATENT DOCUMENTS

| | | | |
|---|---|---|---|
| 3,847,547 | 11/1974 | Delgendre et al. | 337/300 X |
| 4,065,593 | 12/1977 | Peterson | 126/449 X |
| 4,259,543 | 3/1981 | Proud et al. | 337/331 X |
| 4,758,695 | 7/1988 | Sanford et al. | 337/320 X |
| 4,821,997 | 4/1989 | Zdeblick | 251/11 |
| 4,940,896 | 7/1990 | Hagins et al. | 250/338.3 |
| 4,943,032 | 7/1990 | Zdeblick | 251/11 |

OTHER PUBLICATIONS

A resume announcing a conference of the Japan Society of Robot, held Sep. 20-22, 1988, pp. 275-276.
Journal of Japan Society of Robot, vol. 5, No. 2, pp. 3-17, published Apr. 1987 (the last page being an English abstract).

Primary Examiner—Frank Gonzalez
Attorney, Agent, or Firm—Finnegan, Henderson, Farabow, Garrett & Dunner

[57] ABSTRACT

An actuator is comprised of a main body, an inner space filled with an amount of thermally expansive gas and having a first portion in the form of a shallow configuration with an opening oriented toward one side of the main body, a second portion and a bottleneck passage located therebetween, a membrane in the form of a thin film connected to the side of the main body for closing the opening of the first portion of the inner space, a substance for converting the light into heat, and a guide device for guiding light into the second portion of the inner space. Upon an unexpected application of an external force on the thin film, the deformation of the thin film is limited at minimum by being supported by the bottom surface of the first portion. This ensures the prevention of the breakage of the thin film.

4 Claims, 5 Drawing Sheets

LIGHT OPERATED MECHANICAL ACTUATOR

RELATED INVENTION

This is a Continuation-In-Part of pending U.S. application Ser. No. 07/764,677, filed Sep. 25, 1991.

BACKGROUND OF THE INVENTION

The present invention relates to an actuator and in particular to an actuator for operating a relatively minute device such as a catheter, a manipulator for operating the cell or a manipulator for operating a robot to be used in a narrow space.

An actuator of the kind which is disclosed in the foregoing application includes a main body having an inner space in the form of a blind bore with an opening, a thin film member connected to the main body for closing the inner space, an amount of thermally expansive gas filled in the inner space, a substance for converting the light into the heat which is accommodated in the inner space, and a controller having a device for guiding the light into the inner space.

In the foregoing actuator, upon application of the light into the inner space of the main body, heat at a degree is generated, and the resultant heat brings the gas into expansion. Thus, the thin film is deformed and the resultant deformation is set to be used as a force for driving a specific element.

However, since the thin film member is less than 1μ in thickness, if an unexpected external force is applied during construction or usage of the actuator, the thin film may be broken in the worst case.

SUMMARY OF THE INVENTION

It is, therefore, a primary object of the present invention to provide an improved actuator without the foregoing drawback.

It is another object of the present invention to provide an actuator in which a thin film member is prevented form being broken due to an application of an unexpected force thereto.

In order to attain the foregoing objects, an actuator is comprised of a main body, an inner space filled with a thermally expansible gas and having a first portion in the form of a shallow configuration with an opening oriented toward one side of the main body, a second portion and a bottleneck passage located therebetween, a membrane in the form of a thin film connected to the side of the main body for closing the opening of the first portion of the inner space, a substance for converting the light into the heat, and guide means for guiding light into the second portion of the inner space.

BRIEF DESCRIPTION OF THE DRAWINGS

The above and other objects, features and advantages of the present invention will be more apparent and more readily appreciated from the following detailed description of preferred exemplary embodiment of the present invention, taken in connection with the accompanying drawings, in which.

DESCRIPTION OF THE PREFERRED EMBODIMENT

Figure 1:
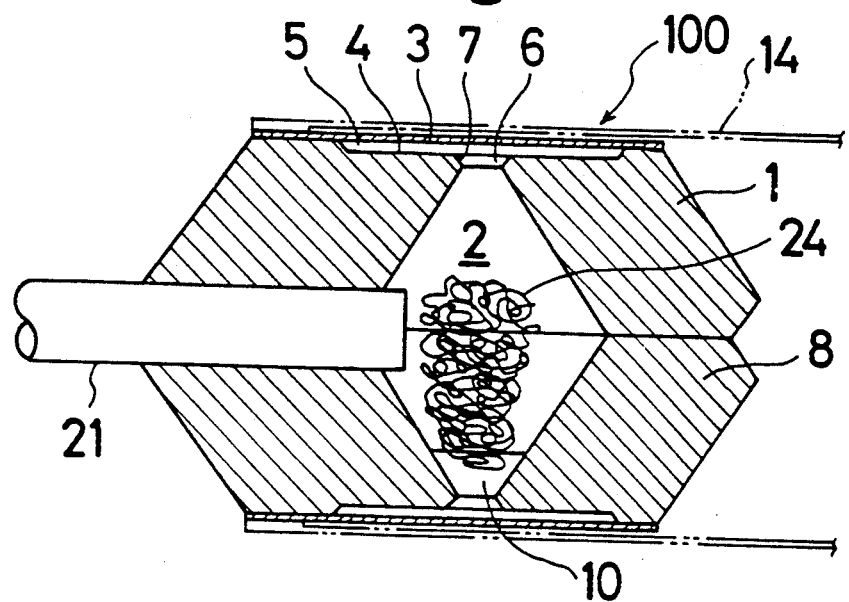
FIG. 1, is an enlarged cross-sectional view of an actuator according to an embodiment of the present invention.
Figure 2:
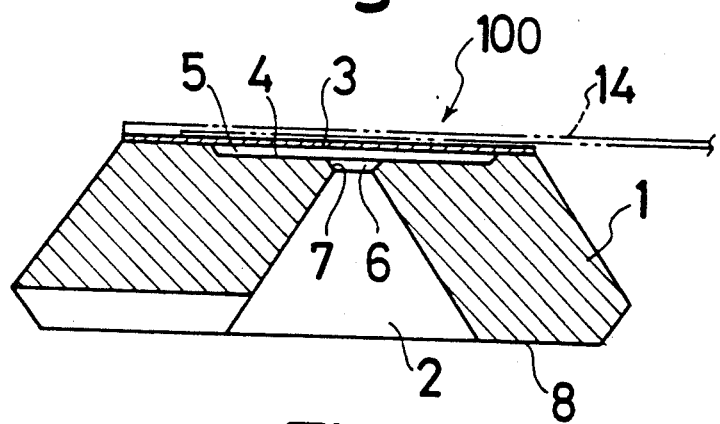
FIG. 2 is a cross-sectional view of an upper half portion of a main body of an actuator.
Figure 3:
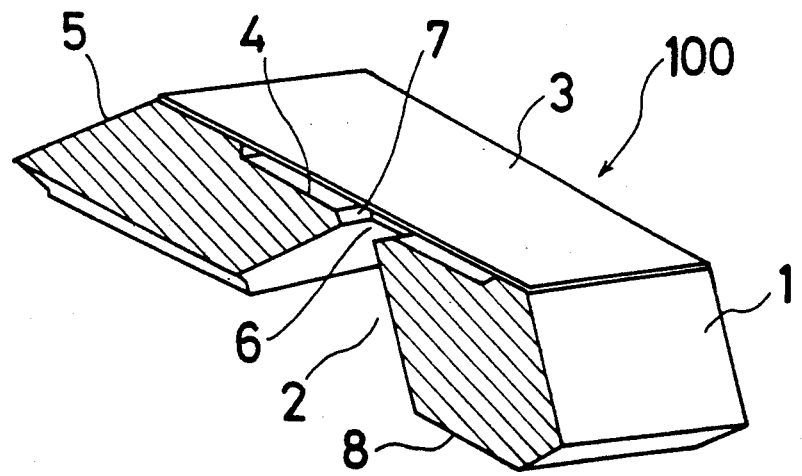
FIG. 3 is another cross-sectional view of an upper half portion of a main body of an actuator for showing an opening of a first portion of an inner space.

Referring to FIGS. 1, 2, 3, 5, 6 and 7, there is illustrated an actuator 100 which is to be used as an extremely miniaturized pincette. The actuator 100 includes a main body which is comprised of a pair of mutually connected members 1 and 8 made of silicon. An inner space is provided in the main body which is filled with gas 10 and carbon fiber 24 as a substance for converting light into heat. As the gas 10, one with a low boiling point is available such as freon-11, freon-113, ethanol, methanol or diethylethanl.

The space defined by the main body includes an inner portion 2 and a pair of outer portions 5. The outer portions 5 are each of a shallow configuration with a flat bottom surface 4 and opens outwardly of the main body. A neck passage 6 is formed at a central portion of the flat bottom surface 4 of the outer portion 5 to establish fluid communication between the outer space portion 5 and the inner space portion 2. The outer periphery of the outer portion 5 is tapered to converge toward the inner space portion 2. The periphery 7 of the neck passage 8 is of a tapered configuration similar to the periphery of the outer portion 5. A membrane 3, in the form of a thin film, is connected to an outer surface of the main body in a manner to close the upper one of the outer space portions 5. A lever 14 is fixed to the membrane 3. Thus, an upper half portion of a minute pincette 200 is established. It is to be noted that a mirror image of the structure of the upper half portion is established at the lower member 8 of the main body as is apparent from the illustrations. A light guiding optical fiber 21 is extended into the inner space portion 2 so as to conduct light from a light source controller 25.

Figure 5:
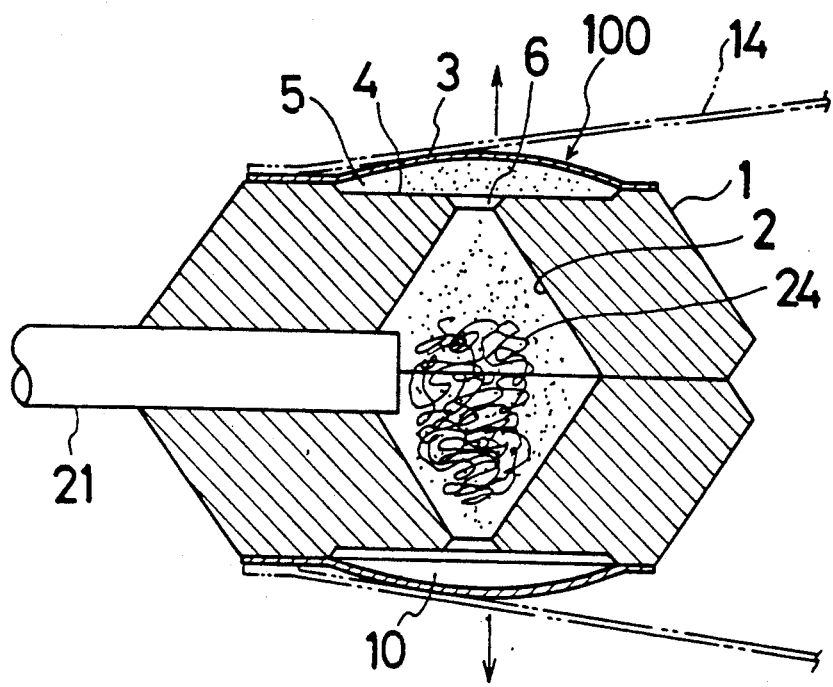
FIG. 5 is a cross-sectional view of an actuator which is in operation.

When the light is transmitted into the inner space 2 from the controller 25 through the optical fiber 21, the carbon fiber 24 is heated to a controlled temperature to heat the gas 10. Then, the gas pressure in the inner portion 2 is increased. The resulting pressure is applied to the membrane 3 after passing through the neck passage 8 and the outer space portion 5. Thus, as shown in FIG. 5, the membrane 3 is deformed in the outward direction together with the lever 14. Since the other lever 14 is brought into a condition similar to the foregoing lever 14, the distance between the levers 14 and 14 is expanded. On the other hand, as soon as the application of the light is interrupted, the pressure drop in the inner space as a result of the temperature decrease therein brings about an inward movement of the membrane 3 to its original position.

Figure 6:
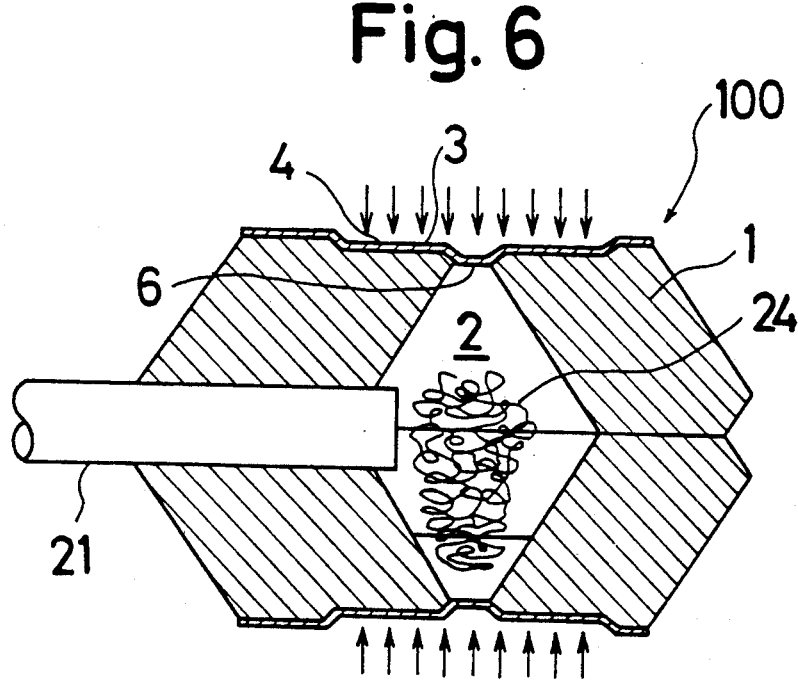
FIG. 6 is a cross-sectional view of an actuator to which an external force is being applied.
Figure 7:
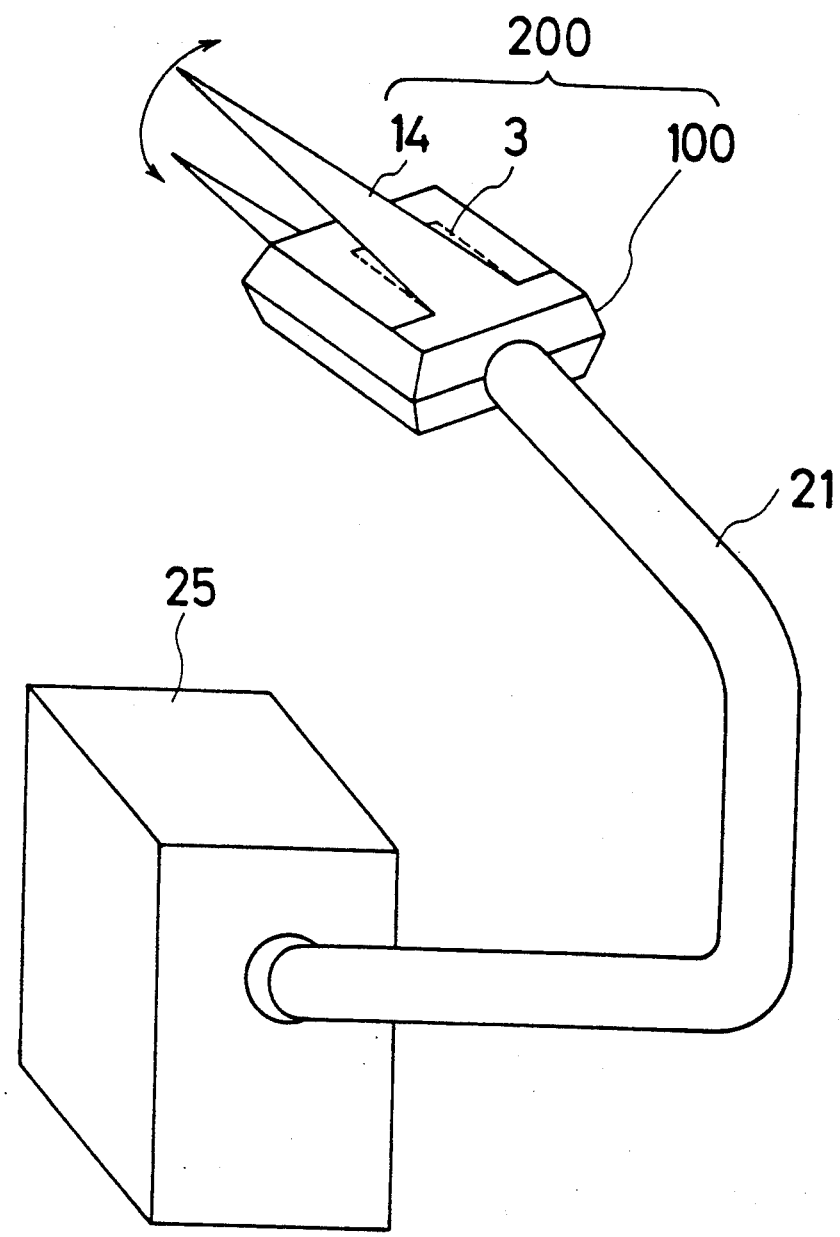
FIG. 7 is a perspective view of an actuator which is used as an extremely miniaturized pincette.

It is to be noted that sometimes an outer external force may be applied unexpectedly to the membrane 3 when the pressure in the inner space is lower than the external force or a mechanical force is applied to the membrane 3 during its manufacturing process, for example. Even though such situation is occurred, the transfer or deformation of the membrane 3 toward the inner space is prevented by the support provided by the bottom surface 4 of the outer space portion 5 as best shown in FIG. 6. In addition, each tapered structure at the periphery of the outer portion 5 and at the neck passage 6 serves to prevent stress concentration in isolated portions of the membrane 3.

The following steps are those of the manufacturing process of the foregoing upper member 1.

Figure 4A:
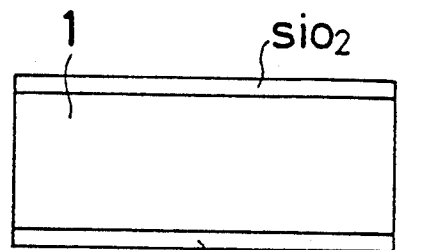
FIGS. 4(a) through 4(l) show a series of steps for producing an upper half portion of an actuator.

(1) First of all, a thin film of silica ($SiO_2$) is formed on a surface of the base plate 1 (FIG. 4a).

Figure 4B:
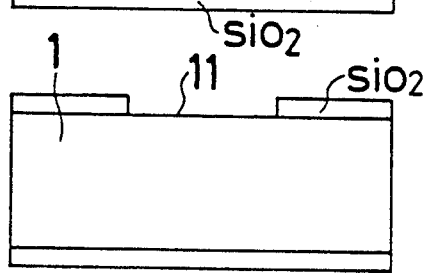

(2) A window 11 in the silica ($SiO_2$) is formed by means of photolithography prior to the establishment of the outer space portion 5 (FIG. 4b).

Figure 4C:
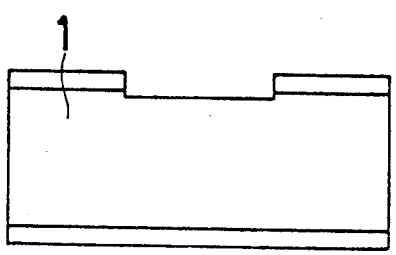

(3) Etching is performed at the window 11 in order to establish the outer portion 5 (FIG. 4c).

Figure 4D:
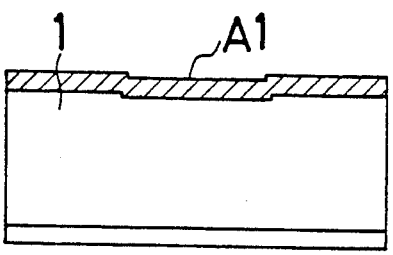

(4) After deletion of surplus thin film of silica ($SiO_2$) upon completion of the etching, a temporary filler of Al is formed on the member 1 by means of the vacuum evaporation method (FIG. 4d).

Figure 4E:
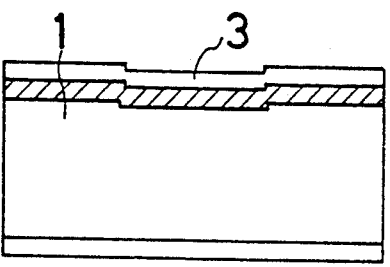
Figure 4F:
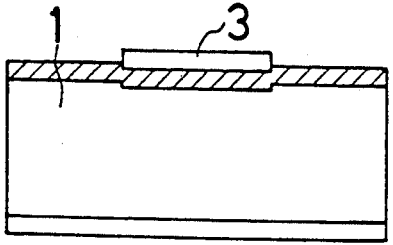
Figure 4G:
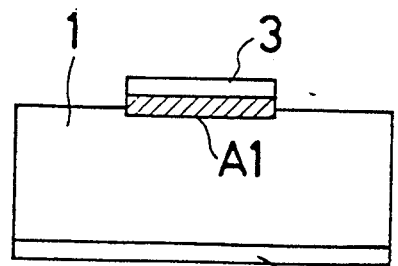

(5) Surplus filler of Al is deleted by using the membrane 3 as a mask (FIGS. 4e through 4g).

Figure 4H:
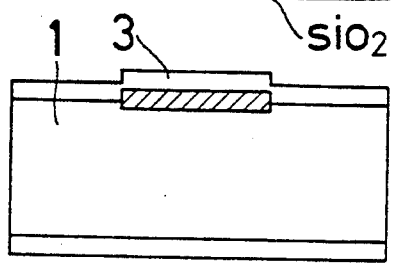

(6) The membrane 3 with a thickness is mounted on the filler of Al (FIG. 4h).

Figure 4I:
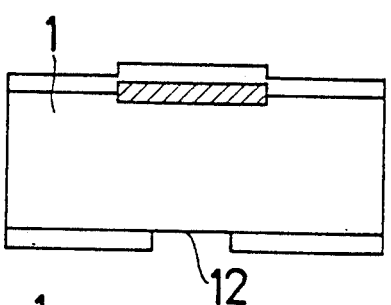
Figure 4J:
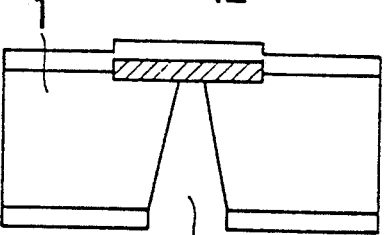

(7) A window in the thin film of silica ($SiO_2$) is formed (FIG. 4i) and the anisotrophy etching is performed for the establishment of the inner portion 2 (FIG. 4j).

Figure 4K:
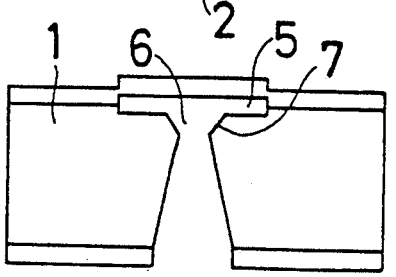

(8) Further anisotrophy etching is performed on the filler of Al for obtaining the outer portion 5 of the inner space and the necked passage 6 with the tapered inner periphery 7 (FIG. 4k).

Figure 4L:
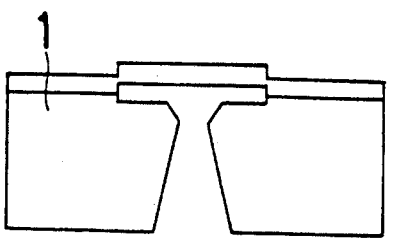

(9) In the last, a thin film of silica ($SiO_2$) is removed (FIG. 4l).

It should be apparent to one skilled in the art that the above-described embodiment is merely illustrative of but a few of the many possible specific embodiments of the present invention. Numerous and various other arrangements can be readily devised by those skilled in the art without departing from the spirit and scope of the invention as defined in the following claims.

What is claimed is:

1. A light operated mechanical actuator comprising:
   a main body having outer surface and an inner space opening through said outer surface;
   a thin film membrane connected to said outer surface and closing said inner space, said inner space being filled with thermally expansible gas and defined by said body to have an inner portion, a shallow outer portion, and a neck passage between said inner portion and said shallow outer portion, whereby inward deflection of the membrane is limited by the depth of said shallow outer portion;
   means for guiding light into the inner portion of said inner space; and
   means for converting light guided into said inner space to heat for expanding the gas therein.

2. An actuator according to claim 1 wherein the shallow outer portion has an inwardly converging tapered peripheral edge.

3. An actuator according to claim 1 wherein the neck passage is delimited by and inwardly converging tapered peripheral edge.

4. An actuator according to claim 1 wherein both the shallow outer portion and the neck portion of the inner space have inwardly converging tapered peripheral edges.

* * * * *